United States Patent
Chomik et al.

(10) Patent No.: US 6,422,091 B1
(45) Date of Patent: Jul. 23, 2002

(54) APPARATUS FOR TESTING THE LIFE EXPECTANCY OF A STRAW

(75) Inventors: Richard S. Chomik, Middlesex; Jacob S. Schmehl, Wayne; Stewart J. Schmehl, U. Mountclair, all of NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/620,187

(22) Filed: Jul. 20, 2000

(51) Int. Cl.⁷ .................................................. G01N 3/20
(52) U.S. Cl. ........................................ 73/851; 73/865.6
(58) Field of Search ........................... 73/826, 831, 833, 73/834, 835, 849, 851, 853, 856, 865.8, 866, 865.6

(56) References Cited

U.S. PATENT DOCUMENTS

| | | |
|---|---|---|
| 1,458,259 A | 6/1923 | Wille |
| 2,764,889 A | 10/1956 | Hughes et al. ............... 73/15.4 |
| 3,793,880 A | 2/1974 | Sugi et al. .................... 73/100 |
| 5,297,440 A | 3/1994 | Rizk et al. .................... 73/849 |
| 5,361,640 A | 11/1994 | Carroll et al. ................. 73/831 |
| 5,442,951 A * | 8/1995 | Gollner et al. ............... 73/40.5 |
| 5,722,219 A * | 3/1998 | Dobransky .................... 53/461 |
| 5,897,013 A | 4/1999 | Manganiello ............... 220/252 |
| 5,979,142 A * | 11/1999 | Kraft et al. .................... 53/410 |

* cited by examiner

*Primary Examiner*—Max Noori
(74) *Attorney, Agent, or Firm*—Ohlandt, Greeley, Ruggiero & Perle LLP (57) ABSTRACT

An apparatus for testing the life expectancy of a straw having a test straw holder, an upper jaw, a lower jaw, and a frame. One end of the test straw is connected to the test straw holder and the other end is disposed between an upper jaw and a lower jaw. The upper jaw is movable along a vertical axis above the straw. The upper jaw engages the straw in a first position and is disengaged from the straw in an second position. The other end of the straw is attached to a pull body. The pull body pulls the straw away from the upper jaw, as the upper jaw engages the straw, to create a pulling stress. The pull body is connected to a grinding rod. The grinding rod pulls the pull body along with the lower jaw sideways as it moves away from the straw to create a grinding stress on the straw. Thus, the apparatus simulates a biting stress, a pulling stress, and a grinding stress on the straw.

19 Claims, 8 Drawing Sheets

APPARATUS FOR TESTING THE LIFE EXPECTANCY OF A STRAW

BACKGROUND OF THE INVENTION

1. Field of the Invention

The present invention relates to an apparatus for testing a straw. More particularly, the present invention relates to an apparatus for testing the life expectancy of a straw or other elastomeric component.

2. Description of the Prior Art

Straws are known in the art for use in connection with drinking cups. Typically, flexible elastomeric straws are used in connection with drinking cups, and together form straw assemblies. These flexible elastomeric components can be made of various materials, such as silicone. One such straw assembly is shown in U.S. Pat. No. 5,897,013 to Manganiello, which issued on Apr. 27, 1999.

The problem is that after continuous biting, pulling, and chewing by consumers on the straw, the straw will break. Thus, the straw is rendered unusable, and the assembly will need to be replaced.

Heretofore, it has been difficult for manufacturers of straws to test the durability of these straws in real life conditions. One problem apparently is that straws undergo several types of stresses created by constant pulling, biting, and grinding by the consumer. Also, consumers will typically chew on the end of the straw creating additional real life stresses. Heretofore, it has been difficult for manufacturers to test the durability of these straws under such realistic conditions.

Accordingly, there is need for an improved method of testing the durability of straws in drinking cup assemblies. In this regard, the present invention is a unique apparatus for testing the durability of a straw or other elastomeric components under real life conditions.

SUMMARY OF THE INVENTION

It is an object of the present invention to provide an apparatus for testing the life expectancy of a straw.

It is another object of the present invention to provide such an apparatus that simulates the realistic stresses placed on a straw by a user.

It is a further object of the present invention to provide such an apparatus that simulates any combination of a biting stress, a pulling stress and a grinding stress on the straw.

These and other objects of the present invention are achieved by a test apparatus that includes a straw holder, a lower jaw, an upper jaw, means for moving the upper jaw away and towards the lower jaw, a pull body assembly, means for moving the pull body assembly in a plane perpendicular to the path of the upper jaw, and a rod.

One end of the straw is attached to the straw holder and the other end is disposed between a movable upper jaw and a movable lower jaw. The upper jaw is movable along an axis towards and away from the lower jaw. The upper jaw engages the straw in a first position and disengages the straw in a second position, thereby creating a biting stress on the straw. The straw holder is attached to an upper portion of a pull body. The pull body is slidable along a straight path in a horizontal plane below the test straw. The pull body is moved concurrently away from the lower jaw as the upper jaw engages the straw so that a pulling stress is applied to the straw. The pull body is attached to a rod. The rod pulls the pull body assembly including the lower jaw sideways off the straight path when the pull body assembly is moved away from the lower jaw, thereby creating a grinding stress on the straw. Thus, the test apparatus simulates a biting stress, a pulling stress and a grinding stress on the straw.

Other and further objects, advantages and features of the present invention will be understood by reference to the following specification in conjunction with the annexed drawings, wherein like parts have been given like numbers.

DESCRIPTION OF THE INVENTION

Figure 1:
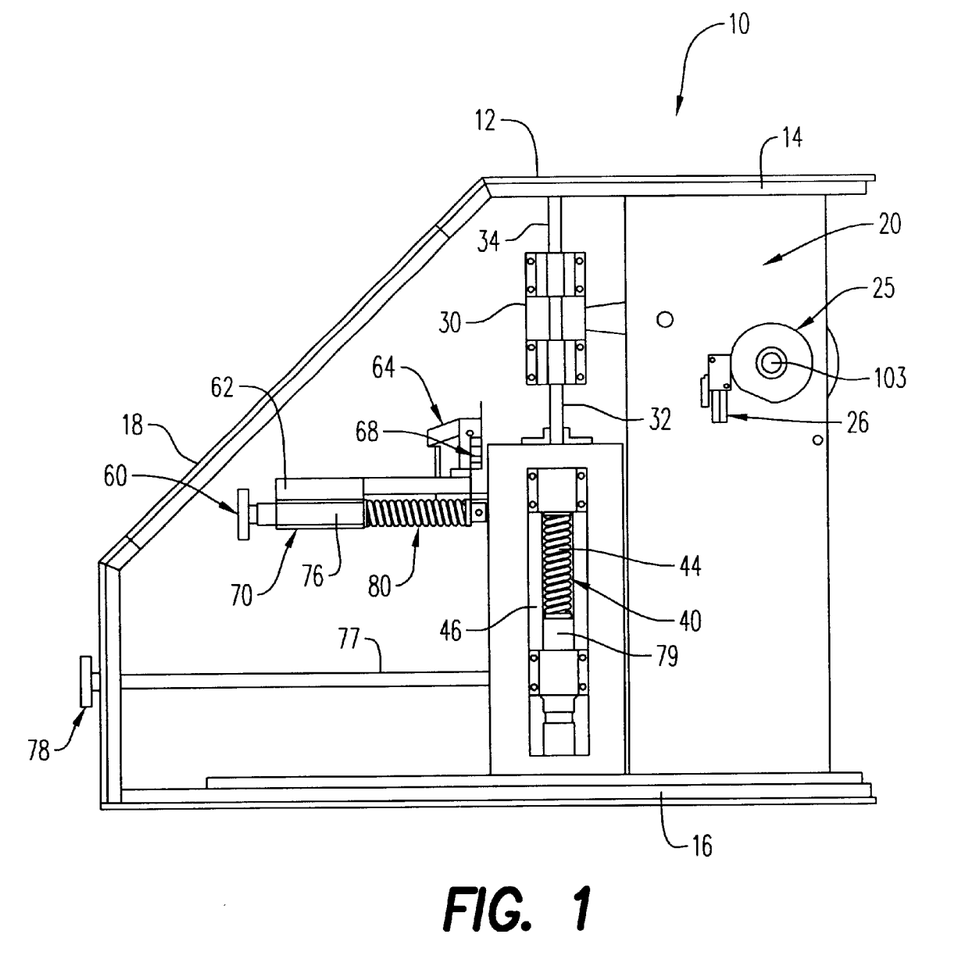
FIG. 1 is a side elevation view of a first side of the apparatus of the present invention.
Figure 2:
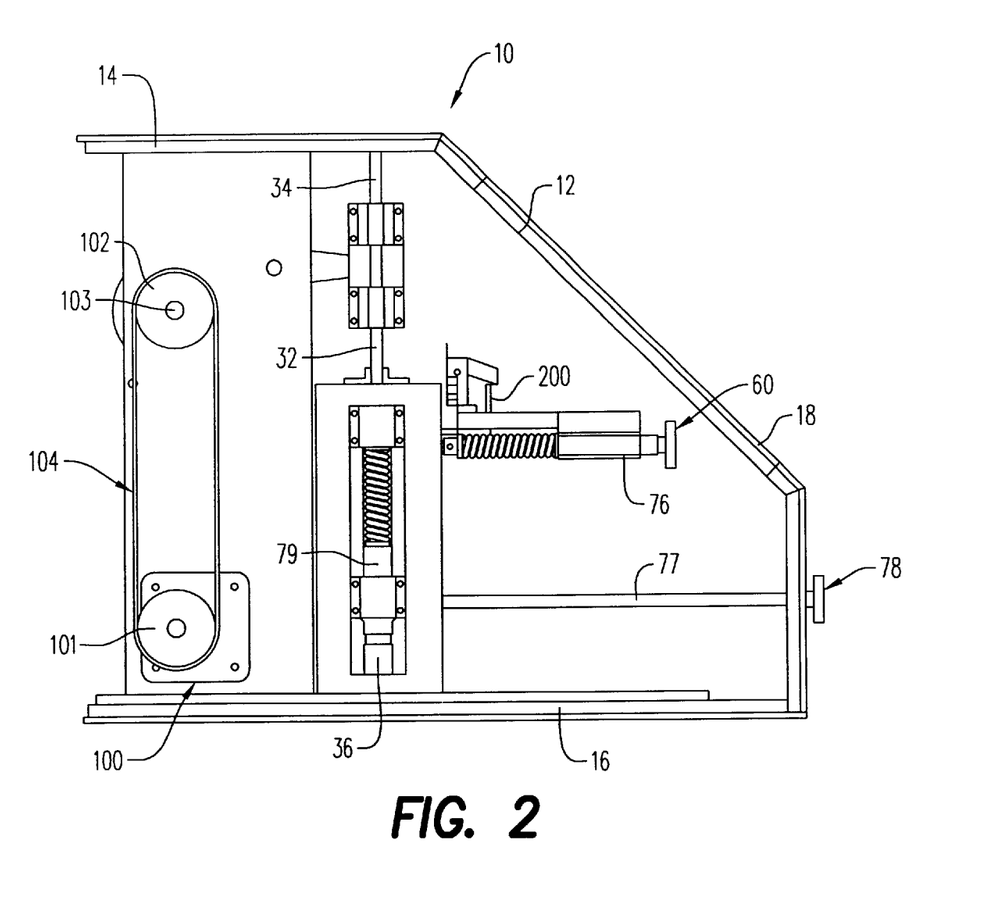
FIG. 2 is a side elevation view of a second side, opposite the first side, of FIG. 1.

Referring to the drawings and, in particular, FIGS. 1 and 2, the apparatus of the present invention is generally referred to by reference numeral 10.

Test apparatus 10, as described, subjects an elastomeric component or test straw 66 (hereinafter "test straw") disposed within the test apparatus to a test cycle having one or more of a jaw closed state, a pulling/grinding state, a relaxed state and a jaw open state that continues until the test straw fails. Thus, test apparatus 10 simulates a biting stress, a pulling stress, and a grinding stress on test straw 66.

Test apparatus 10 has a housing or body 12. Housing 12 has a top surface 14, a bottom surface 16, and front surfaces 18.

Inside of housing 12, there is positioned a frame assembly 20. Frame 20 is disposed in housing 12. Frame 20 includes a shaft assembly 30, a lower jaw housing assembly 40, and a pull body assembly 60.

As shown in FIGS. 1 through 4, shaft assembly 30 includes a shaft 32 having a top portion 34 and a bottom portion 36. The top portion 34 is connected to top surface 14 of housing 12. The bottom portion 36 is disposed through lower jaw assembly 40 and, in particular, through a jaw channel 46, and is connected to bottom surface 16 of housing 12.

Figure 3:
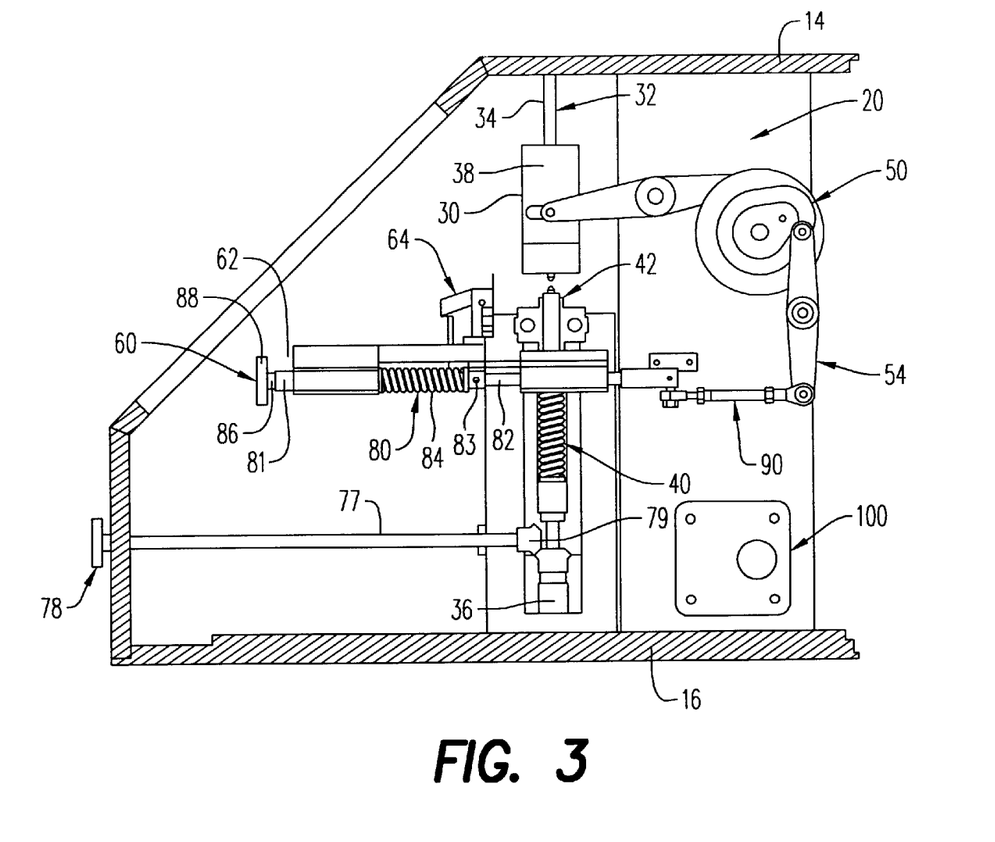
FIG. 3 is a cut-away side elevation view about one-third in of the first side of FIG. 1.

Top portion 34 of shaft 32 has an upper jaw 38, shown clearly in FIG. 3, secured thereto. Bottom portion 36 of shaft 32 has a lower jaw 42 of lower jaw assembly 40 secured thereto. The upper jaw 38 and lower jaw 42 can slide along the central axis of shaft 32. However, in a preferred embodiment, with spring 44 of lower jaw 42 loaded in the direction of upper jaw 38, the upper jaw is adapted to slide towards and away from the lower jaw.

Referring to FIGS. 1 through 4, pull body assembly 60 has an upper portion 62 and a hollow, lower portion 70. Upper portion 62 is connected to a straw holder 64, which is preferably positioned on the upper portion. Holder 64 permits test straw 66 to enter an area between upper jaw 38 and lower jaw 42. In the preferred embodiment, test straw 66 is basically positioned on lower jaw 42. Also, connected to upper portion 62 is a stop switch 68.

Figure 4:
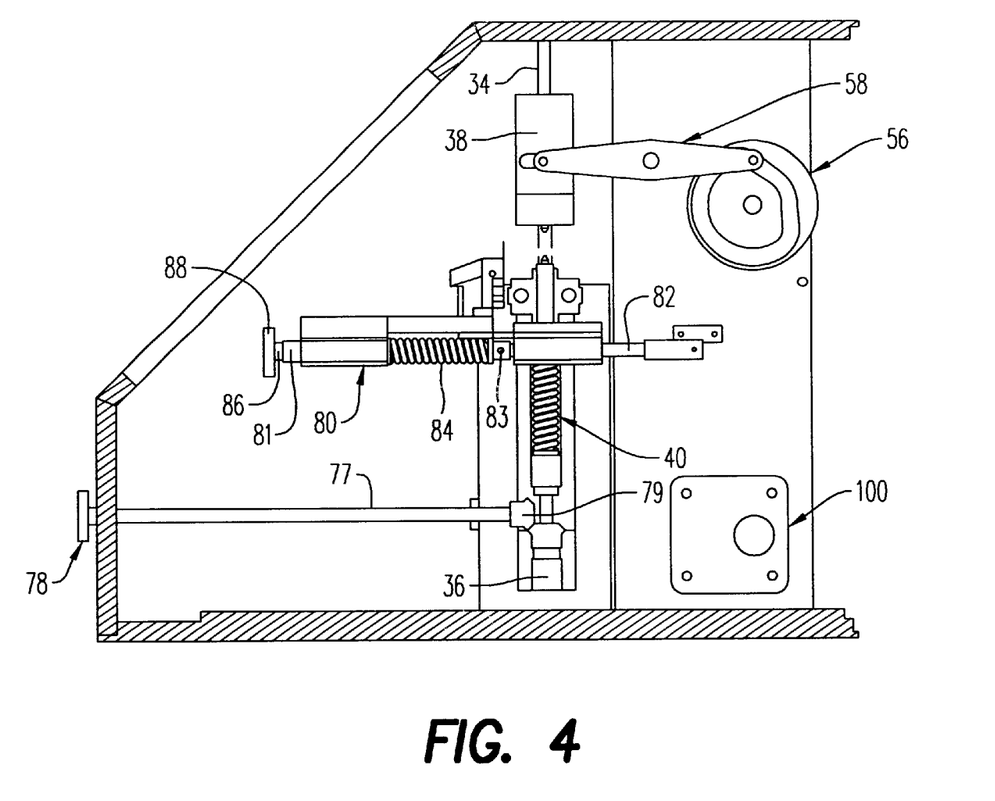
FIG. 4 is a cut-away side elevation view about two-thirds in of the first side of FIG. 1.

Hollow, lower portion 70 has a sleeve 76 that is adapted to receive and hold a portion of shaft assembly 80. As shown in FIGS. 3 and 4, shaft assembly 80 has a shaft 86. About shaft 86 is a compression spring 84, and a pair of rods 81, 82, each positioned on either side of the compression spring. The shaft assembly 80 extends along a horizontal plane and is perpendicular to shaft 32.

Rod 82 has a shoulder 83 that has a larger diameter than the inside diameter of compression spring 84 so that the compression spring presses against shoulder 83. Rod 81 has a diameter larger than the diameter of compression spring 84 so that compression spring 84 must remain between the two rods 81, 82. The free end of shaft 86 is connected to a handle 88, and the other end of the shaft passes through lower jaw housing assembly 40 and shaft 32 and is connected to a connecting rod 90 as shown in FIG. 3. Handle 88 is adapted to rotate shaft 86 to push rod 81 against compression spring 84 thereby compressing the spring. Compression spring 84, when compressed, sets the pulling force to be applied to test straw 66 described below.

Figure 5:
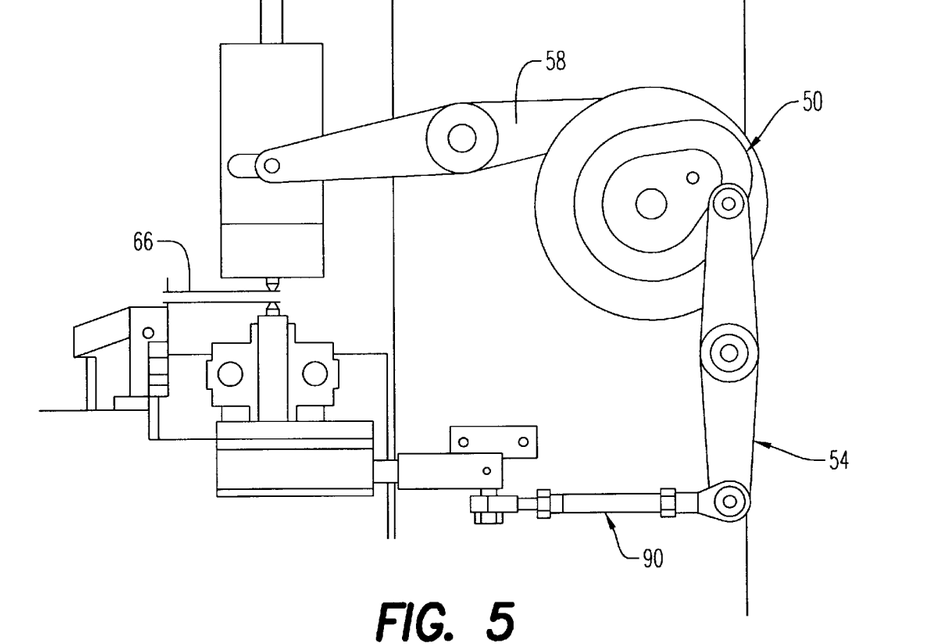
FIG. 5 is an enlarged view of the pull cam shown in FIG. 3.

Referring to FIGS. 3 and 5, pull cam 50 is an eccentric cam that contacts first lever 54. First lever 54 is operatively connected to connecting rod 90. Referring to FIG. 2, a motor 100, through drive gear 101, drive chain 104 and driven gear 102 shown in FIG. 2, drives pull cam 50 to act on first lever 54.

Figure 6:
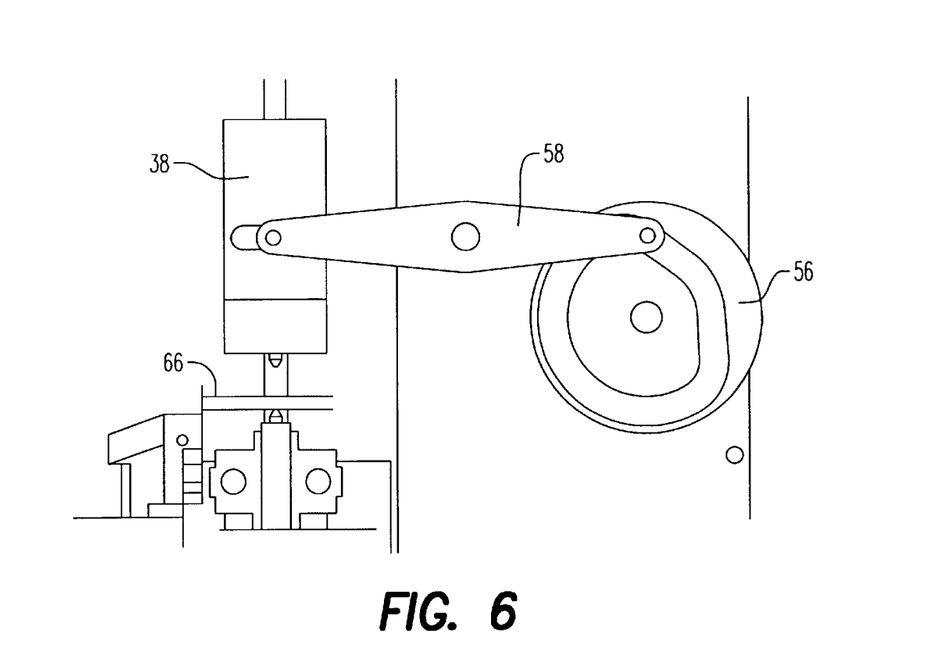
FIG. 6 is an enlarged view of the bite cam shown in FIG. 4.

Referring to FIGS. 4 and 6, upper jaw 38 is connected by a second lever 58 to a bite cam 56. The bite cam 56 is, in turn, connected to motor 100 through drive chain 104 shown in FIG. 2. Bite cam 56 through second lever 58 immediately causes upper jaw 38 to descend thereby clamping the straw against lower jaw 42, beginning the test cycle. Second lever 58 then enters a dwell period for bite cam 56. At this time, pull cam 50 through first lever 54 and connecting rod 90 compresses compression spring 84 causing a pulling force to be applied to the straw.

Figure 7:
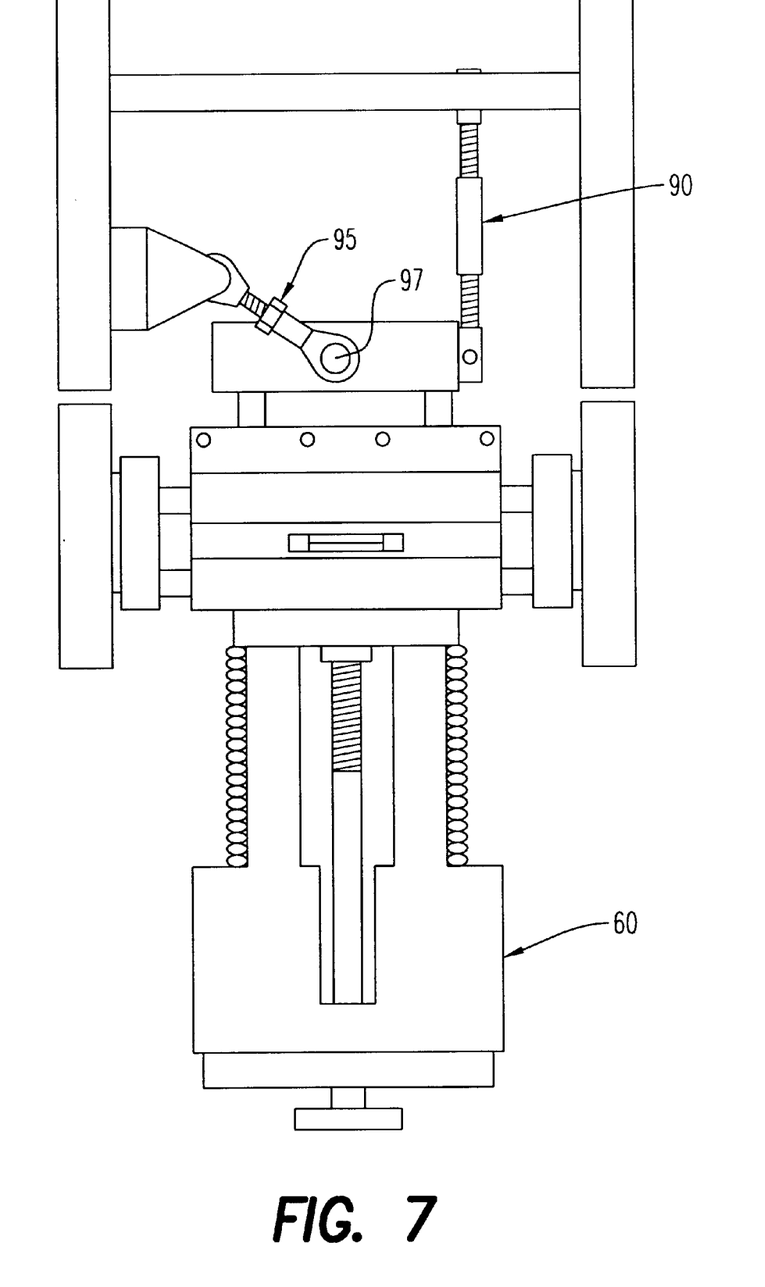
FIG. 7 is a partial top view of the apparatus of FIG. 1.

Referring to FIG. 7, the forward motion of connecting rod 90 and pull body assembly 60 causes a rod 95 to pull the pull body assembly 60 sideways. Since pull body assembly 60 is connected to lower jaw 42, the lower jaw is moved sideways causing a grinding motion on the straw. Pull body assembly 60 is attached to rod 95 at pivot 97. Rod 95 is pivotally attached to body 12 at about a ninety-four degree angle to the horizontal axis of pull body assembly 60. Thus, when pull body assembly 60 is moved along the straight path between its relaxed position and its compressed position, rod 95 pulls the pull body assembly 60 sideways off this straight path. Pull body assembly 60 is returned to this straight position in relaxed position. Thus, rod 95 creates a grinding motion when pull body assembly 60 is moved between its compressed and relaxed positions.

As the test cycle continues pull cam 50 provides for a complete relaxation of pull on test straw 66 before bite cam 56 causes upper jaw 38 and lower jaw 42 to separate apart. This test cycle repeats until test straw 66 breaks. Straw holder 64, with pull body assembly in its relaxed position, is held erect by roller 200, shown in FIG. 2. With no resulting reaction by the now broken straw 66, straw holder 64 is free to rotate, by gravity, allowing switch 68 to move to its normal position thereby actuating switch 68. Referring to FIG. 1, the lack of resulting action by the now broken straw 66 also enables the actuation of switch 26 through a cycle cam 25 causing motor 100 to stop, ending the test cycle. Motor 100 stops because switch 66 and switch 26 are electrically in parallel. Thus, the deactivation of both switches stops motor 100. Therefore, switch 68 and switch 26 ensure that motor 100 will only stop when cycle cam 25 is in a position corresponding to upper jaw 30 being in the open position which facilitates the removal of and replacement of test straw 66.

Referring to FIGS. 1 through 4, upper jaw 38 engages test straw 64 at a first position shown in FIGS. 5 and 6, and disengages from the test straw at second position shown in FIGS. 3 and 4. The engagement and disengagement simulates a biting stress on test straw 66. As mentioned before, lower jaw 42 is held stationary. When upper jaw 38 engages test straw 66 in the first position some of the impact is absorbed by spring 44 of lower jaw assembly 40, so that lower jaw 42 descends slightly down the vertical axis.

The pressure of spring 44 against lower jaw 42 can be increased or decreased by turning a first pressure setting knob 78, which is connected to rod 77, and in turn to a collar 79 to apply or release compression of spring 44. For example, first pressure setting knob 78 can be rotated clockwise so that collar 79 is moved towards upper jaw 38 and the pressure of spring 44 is increased against lower jaw 42, or first pressure setting knob 78 can be rotated counterclockwise so that collar 79 is moved away from the upper jaw. Accordingly, the parameters of test apparatus 10 can be quickly changed to create more or less biting stress on test straw 66.

It should be noted that a combination of strain gauges and readouts are provided for the user to precisely set the desired settings, such as the pulling force which is set via handle 88 acting on compression spring 84 and the biting stress which is set via first pressure setting knob 78 acting on spring 44.

Rod 81 is moved concurrently into compressed spring 84 as upper jaw 38 is moved into its first position. As upper jaw 38 engages test straw 66 in its first position, pull body assembly 60 is moved along a horizontal axis away from upper jaw 38, thereby creating a pulling stress on test straw 66. Thus, test apparatus 10 simultaneously creates a biting stress and a pulling stress on test straw 66.

Also, rod 95 creates a grinding stress on test straw 66 as pull sleeve assembly 60 is moved concurrently into its compressed position and upper jaw 38 is moved into its first position. Thus, test apparatus 10 simultaneously creates a biting stress, pulling stress, and grinding stress on test straw 66.

Referring again to FIG. 2, motor 100 is preferably connected to body 12. Upper jaw 38 is moved between first position and second position by motor 100 activating drive gear 101 to move drive chain 104, which moves driven gear 102. Driven gear 102 is fixed to cam drive shaft 103.

Switch 68 and switch 26 cut off the electrical output to motor 100 when the stop switch 68 is disengaged from straw holder 64. Thus, motor 100 continues to drive a cam drive shaft 103 while test straw 66 and stop switch 68 are engaged. The testing apparatus continues to apply biting stress, pulling stress, and grinding stress on test straw 66 until the test straw breaks in two pieces. At which point, pull body assembly 60 falls back. Straw holder 64 disengages from stop switch 68 along with switch 26 in this fall back position, thereby cutting off the electrical output to motor 100 and ending the test cycle.

Figure 8:
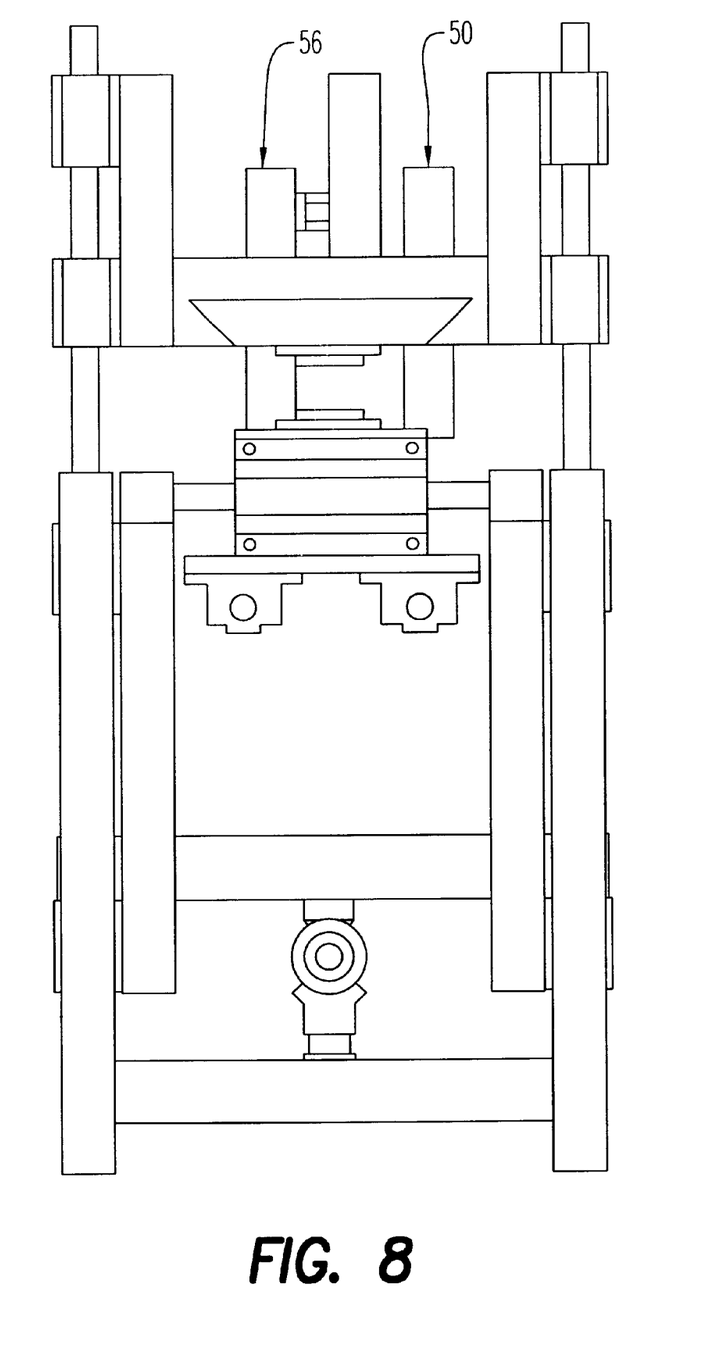
FIG. 8 is a partial front view of the apparatus of FIG. 1.

Referring to FIG. 8, it shows the positions of pull cam 50 and bite cam 56. Pull cam 50 and bite cam 56 are fixed on cam drive shaft 103. Also fixed to cam shaft 103 is driven gear 102. Motor 100 activates drive gear 101 to move drive chain 104 which moves driven gear 102. Driven gear 102 moves cam drive shaft 103 to move pull cam 50 and bite cam 56.

Figure 9:
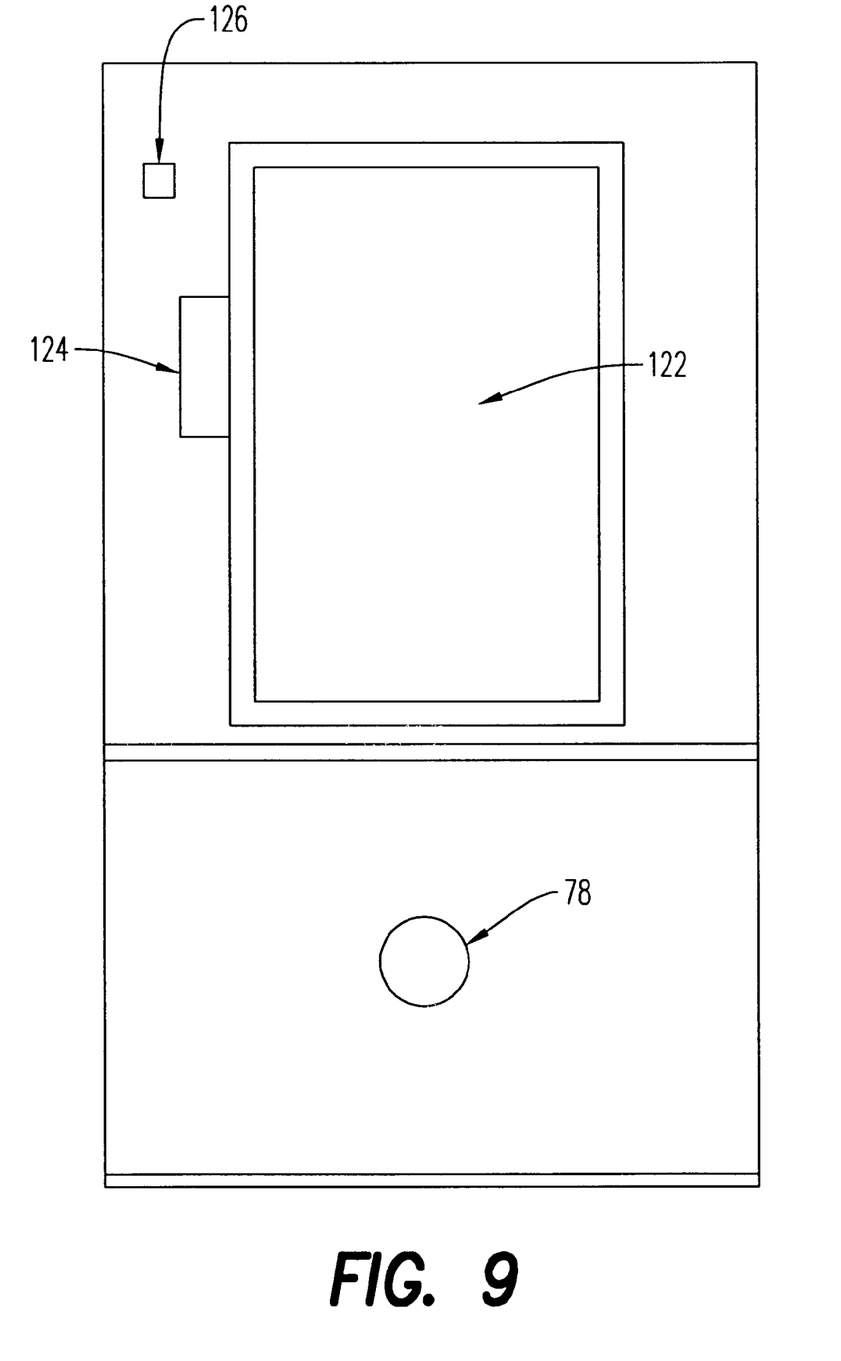
FIG. 9 is a front view of the apparatus of FIG. 1.

Referring to FIG. 9, front surface 18 of body 12 has an access window 122 and a start button 126. Access window 122 is attached to housing 12 preferably by hinges on the right side of access window 122. Start button 126 is preferably a pressure switch that can be pushed and electrical power then supplied to motor 100.

Electrical interlock 124 engages a switch (not shown) on housing 12 when access window 122 is closed so that electrical power is supplied to motor 100. Electrical interlock 124 disengages the switch on housing 12 when access window 122 is swung open, thereby cutting off electrical power to motor 100. Thus, when personnel are inserting or removing test straw 66, access window 122 can simply be opened and motor 100 is shut down, thereby preventing injuries from the biting, pulling, and grinding stresses of testing apparatus 10.

The present invention having been described with particular reference to the preferred forms thereof, it will be obvious that various changes and modifications may be made therein without departing from the spirit and scope of the present invention as defined in the appended claims.

What is claimed is:

1. An apparatus for testing the life expectancy of a straw having a biting end and a pulling end, said apparatus comprising:
    a frame having a shaft assembly, a lower jaw assembly, a pull body, and first means for moving an upper jaw,
    said shaft assembly having said upper jaw,
    said lower jaw assembly having a lower jaw,
    said pull body assembly having a test straw holder, said test straw holder being adapted to receive the pulling end of the straw such that the biting end is disposed between said upper and lower jaws,
    wherein said upper and lower jaws are connected to said shaft assembly to slide along a vertical axis,
    wherein said first moving means is connected to said frame and is adapted to move said upper jaw between a first position and a second position along said vertical axis, and
    wherein first moving means slides said upper jaw to engage the biting end of the straw between said upper jaw and said lower jaw at said first position and slides said upper jaw to disengage from the biting end at said second position, thereby simulating a biting stress on the straw.

2. The apparatus according to claim 1,
    wherein said pull body assembly has an upper portion, a lower portion, and a shaft, said lower portion having a front side, a back side, and a channel extending therethrough, said channel being adapted to receive said shaft such that said pull body assembly is slidable along said shaft in a straight path along a horizontal plane between a compressed position and a relaxed position; and wherein
    said test straw holder is connected to said upper portion of said pull body assembly, said pull body assembly pulling the straw away from said lower jaw in said compressed position, and moving toward said lower jaw in said relaxed position;
    the apparatus further comprising second means, attached to said frame, for moving said pull body assembly between said compressed position and said relaxed position, thereby simulating a pulling stress on the straw.

3. The apparatus according to claim 2, wherein said first moving means has a first motor means, and wherein said second moving means has a second motor means.

4. The apparatus according to claim 2, wherein said pull body assembly has:
    a grinding rod having a first connecting end and a second connecting end, said first connecting end being pivotally connected to said pull body assembly, said second connecting end being pivotally connected to said frame, wherein said grinding rod is connected to said pull body assembly at an angle to said straight path, and
    wherein said grinding rod pulls said pull body assembly sideways as said pull body assembly is moved from said relaxed position to said compressed position, thereby creating a grinding stress on the straw.

5. The apparatus according to claim 4, wherein said upper jaw and said pull body assembly are moved concurrently into said first position and said compressed position, thereby simultaneously simulating said biting stress, said pulling stress, and said grinding stress.

6. The apparatus according to claim 3, further comprising:
    a stop switch for engaging said test straw holder when the straw is attached to said test straw holder, wherein said stop switch supplies electrical power to said first motor means and disengages said test straw holder when the straw breaks in half, and cuts off said electrical power to said second motor means thereby ending the test.

7. The apparatus according to claim 1, wherein said shaft assembly has a bite shaft connected to said frame, said upper jaw being connected to an upper portion of said bite shaft to slide along said vertical axis, and said lower jaw being connected to a lower portion of said bite shaft to slide along said vertical axis, wherein said lower jaw sits on top of a bite spring such that when said upper jaw engages the straw in said first position said lower jaw is pushed against said bite spring, thereby relieving said biting stress on the straw.

8. The apparatus according to claim 7, further comprising:
    a rotatable pressure knob that when rotated in a first direction causes said bite spring to increase said biting stress, and when rotated in a second direction causes said bite spring to decrease said biting stress.

9. The apparatus according to claim 1, wherein the straw is a silicone straw.

10. A method of testing the life expectancy of a straw, wherein the straw has a first end and a second end opposite the first end, said method comprising the steps of:
    (a) disposing the first end between an upper jaw and a lower jaw;
    (b) pressing said upper jaw and said lower jaw together so as to engage the first end of the straw; and
    (c) separating said upper jaw and said lower jaw, thereby simulating a biting stress on the straw until the straw breaks, thereby determining the life expectancy of the straw.

11. The method of claim 10, further comprising the step of pulling the second end of the straw along a straight path in a horizontal plane away from said upper jaw and said lower jaw during step (b), thereby creating a pulling stress on the straw.

12. The method of claim 10, wherein the second end of the straw is pulled along a curved path from a relaxed position to a compressed position so that a grinding stress is created on the straw.

13. A method of testing the life expectancy of a straw, wherein the straw has a first end and a second end opposite the first end, said method comprising the steps of:
   (a) disposing the first end between an upper jaw and a lower jaw;
   (b) pressing said upper jaw and said lower jaw together so as to engage the first end of the straw;
   (c) disposing the second end of the straw in a holder; and
   (d) pulling the second end of the straw along a straight path in a horizontal plane away from said upper jaw and said lower jaw thereby creating a pulling stress on the straw until the straw breaks, thereby determining the life expectancy of the straw.

14. The method of claim 13, further comprising the step of separating said upper jaw and said lower jaw to simulate a biting stress on the straw.

15. The method of claim 13, wherein the second end of the straw is pulled along a curved path from a relaxed position to a compressed position so that a grinding stress is created on the straw.

16. A method of testing the life expectancy of a straw, wherein the straw has a first end and a second end opposite the first end, said method comprising the steps of:
   (a) disposing the first end between an upper jaw and a lower jaw;
   (b) pressing said upper jaw and said lower jaw together so as to engage the first end of the straw;
   (c) disposing the second end of the straw in a holder; and
   (d) pulling the second end of the straw along a curved path from a relaxed position to a compressed position so that a grinding stress is created on the straw until the straw breaks, thereby determining the life expectancy of the straw.

17. The method of claim 16, further comprising the step of separating said upper jaw and said lower jaw to simulate a biting stress on the straw.

18. The method of claim 16, further comprising the step of pulling the second end of the straw along a straight path in a horizontal plane away from said upper jaw and said lower jaw during step (b), thereby creating a pulling stress on the straw.

19. The method of claim 16, further comprising the step of repeating steps (a) through (c) until the straw breaks.

* * * * *